(12) United States Patent
Cauthen

(10) Patent No.: US 6,520,967 B1
(45) Date of Patent: Feb. 18, 2003

(54) SPINAL IMPLANT INSERTION INSTRUMENT FOR SPINAL INTERBODY PROSTHESES

(75) Inventor: Joseph C. Cauthen, Gainesville, FL (US)

(73) Assignee: Cauthen Research Group, Inc., Gainesville, FL (US)

( * ) Notice: Subject to any disclaimer, the term of this patent is extended or adjusted under 35 U.S.C. 154(b) by 0 days.

(21) Appl. No.: 09/570,648

(22) Filed: May 15, 2000

Related U.S. Application Data
(60) Provisional application No. 60/160,711, filed on Oct. 20, 1999.

(51) Int. Cl.[7] .............................................. A61B 17/58
(52) U.S. Cl. ............................ 606/99; 606/86; 606/90; 606/96; 600/219; 600/235
(58) Field of Search ............................. 606/53, 90, 57, 606/86, 60, 61, 99, 104; 600/201, 204–206, 210, 213–216, 218–222, 224–226, 235; 623/17.16

(56) References Cited

U.S. PATENT DOCUMENTS

| | | | |
|---|---|---|---|
| 3,916,907 A | 11/1975 | Peterson | 128/345 |
| 4,545,374 A * | 10/1985 | Jacobson | 128/303 |
| 4,772,287 A | 9/1988 | Ray et al. | 623/17 |
| 4,898,161 A | 2/1990 | Grundei | 606/105 |
| 5,015,247 A | 5/1991 | Michelson | 606/61 |
| 5,020,519 A * | 6/1991 | Hayes et al. | 128/96 |
| 5,431,658 A | 7/1995 | Moskovich | 606/99 |
| 5,484,437 A | 1/1996 | Michelson | 606/61 |
| 5,540,697 A * | 7/1996 | Rehmann et al. | 606/91 |
| 5,720,751 A * | 2/1998 | Jackson | 606/86 |
| 5,741,253 A | 4/1998 | Michelson | 606/61 |
| 5,755,732 A | 5/1998 | Green et al. | 606/170 |
| 5,785,647 A | 7/1998 | Tompkins et al. | 600/201 |
| 5,797,909 A | 8/1998 | Michelson | 606/61 |
| 5,803,904 A | 9/1998 | Mehdizadeh | 600/235 |
| 5,885,300 A | 3/1999 | Tokuhashi et al. | 606/99 |
| 6,080,155 A | 6/2000 | Michelson | 600/61 |
| 6,096,044 A * | 8/2000 | Boyd et al. | 606/96 |

FOREIGN PATENT DOCUMENTS

| | | |
|---|---|---|
| EP | 739614 A | 10/1996 |
| WO | 9801091 | 1/1998 |
| WO | 9817209 | 4/1998 |
| WO | 0001293 | 1/2000 |

* cited by examiner

Primary Examiner—David J. Isabella
Assistant Examiner—Umi Chattopadhyay
(74) Attorney, Agent, or Firm—Saliwanchik, Lloyd & Saliwanchik (57) ABSTRACT

A spinal implant insertion instrument for intervertebral implant surgery formed from a hollow first element of various external diameters, including a channel to accommodate and incorporate a vertebral pedicle, and a second element joined by a hinge to the first element, allowing reduction of the external diameter of the leading edge of the spinal implant insertion element sufficient to allow the passage of the spinal implant insertion instrument into the inteivertebral disc space in a safe fashion, as the first maneuver, to be followed by activation of the second element upon the first, restoring the internal diameter of the spinal implant insertion instrument to a sufficient radius to allow successive passage of cutting, reaming, tapping instruments, and subsequent implantation of a spinal interbody implant device. The design of this instrument reduces traction uponsensitive neural elements, allows controlled removal of the medial portion of the vertebral pedicle, distracts the intervertebral disc space, and allows safe passage of reaming, tapping, and spinal implant insertion devices through the expanded bore of the spinal implant insertion instrument.

10 Claims, 11 Drawing Sheets

SPINAL IMPLANT INSERTION INSTRUMENT FOR SPINAL INTERBODY PROSTHESES

CROSS-REFERENCE TO A RELATED APPLICATION

This application claims the benefit of U.S. Provisional Application No. 60/160,711, filed Oct. 20, 1999.

FIELD OF THE INVENTION

The invention relates generally to a spinal implant instrument for use in intervertebral spinal fusions, and more specifically, to an improved method of protection for neural elements during intervertebral disc space distraction, disc space reaming and tapping, and placement of intervertebral disc space bone grafts and prosthetic devices.

BACKGROUND OF THE INVENTION

The spinal column is formed from a number of vertebrae, which in their normal state, are separated from each other by cartilaginous intervertebral discs. These discs form a cushion between adjacent vertebrae, resisting compression along the support axis of the spinal column, but permitting limited movement between the vertebrae to provide the characteristic flexible movement of the healthy spine. Injury, disease, or other degenerative disorders may cause one or more of the intervertebral discs to shrink, collapse, deteriorate, or become displaced, herniated, or otherwise damaged.

Intervertebral stabilization by fusion of adjacent vertebrae has proven successful in permanently preserving intervertebral spacing. However, a number of technical barriers exist, including, for example, the retraction of neural elements out of the normal anatomic position, to a temporarily disadvantageous position, to allow reaming, tapping, and insertion of various intervertebral disc space bone grafts and prostheses. The displacement of neural elements (nerve roots) in such fashion is not uncommonly followed by temporary, or even permanent injury to the nerve roots. This can present an unpleasant, nearly intolerable burning pain in the extremities. Also, traumatic openings in the nerve covering may occur, allowing the escape of cerebral spinal fluid, and requiring with subsequent repair, resulting scar and nerve restriction. There may also be disruption of motor and sensory nerve elements, potentially causing permanent numbness and weakness in the extremities, bladder, bowel, or genitalia.

Attempts to minimize the disadvantageous effects of retraction of neural elements include various nerve root retractors, designed to facilitate placement of the insertion tools against the adjacent nerves, and are commercially available. One disadvantage of these hand held retractors is instability. This instability may be caused by movement of the retractors by the insertion tools or by the shifting attention of the surgical assistant responsible for holding the retractors. Also, the physical bulk of the retractors themselves requires additional space in the limited confines of the intervertebral disc space being prepared for the intervertebral body prosthesis. In view of this, a need exists for a spinal implant insertion instrument to eliminate the need for separate nerve root retractors, and to protect neural elements from injury by the sequence of insertion tools as outlined above.

A need further exists for such a device designed for easy insertion, combining protection and nerve root retraction, at the same time speeding up the entire operative procedure in a safe and efficient manner.

Still another need exists for a method of distraction of the intervertebral disc space prior to insertion of the improved spinal implant. It is to that provision, for a device and method meeting these and other needs, that the present invention is primarily directed.

BRIEF SUMMARY OF THE INVENTION

The subject invention provides a means for the protection of the nerve root during the insertion of a spinal implant on bone graft into an intervertebral disc space. Briefly described, in a preferred form, the present invention comprises a spinal implant insertion instrument, generally comprising a hollow body with an outer surface and an open interior surface. A fixed conically shaped curved guide with straight concave or convex contours extends from the bottom end of the hollow body. Additionally, a handle element, with a retractable conically shaped curved guide, is pivotally attached to the bottom end of the hollow body with an adjustable articulating hinge. The handle element is attached to the hollow body such that the retractable curved guide is positioned on an opposite side of the hollow body as the fixed curved guide. The cross-sectional area of the hollow body can be rectangular, elliptical or other shape, so long as it is of sufficient size to allow passage of instruments for reaming, tapping, and placement of intervertebral bone grafts or prosthetic devices.

In an alternative form, stringer elements are affixed to the outer surface of the fixed curved guides, where the stringer elements traverse the lengths of the curved guides. The stringer elements add additional strength to the curved guides.

In a preferred form, the spinal instrument comprises a primary locking mechanism. The primary locking mechanism locks the curved guides in the fully extended position by securing the handle element to the hollow body. Preferably, the locking mechanism is a spring-loaded retraction ring, which locks and secures the handle element by engaging a locking tab, which extends from the handle proximal end.

The spinal implant insertion instrument can be fabricated from biocompatible materials including, without limitation, titanium, surgical alloys, stainless steel, or any other material suitable for fabrication of surgical instruments.

In a preferred method use, the curved guides are positioned between a first vertebra and a second vertebra, with the curved guides being in the un-retracted position. The outer surface of the fixed curved guide is positioned against the lumbar dural tube. The hinged joint allows simultaneous retraction of the nerve root by compressing the handle element into the hollow body. The simultaneous retraction of the nerve root away from the lumbar dural tube allows for a safe retraction of the neural elements, eliminating the need for an independent retraction means, which would add additional bulk in a confined space, which in the present art, contributes to inappropriate compression of neural elements. In the retracted position, the internal diameter of the hollow body is sufficient to allow passage of instruments for reaming, tapping, and placement of intervertebral bone grafts or prosthetic devices.

These and other objects, features and advantages of the present invention will be more readily understood, with reference to the detailed description below, read in conjunction with the accompanying drawings.

DETAILED DISCLOSURE OF THE INVENTION

Figure 1:
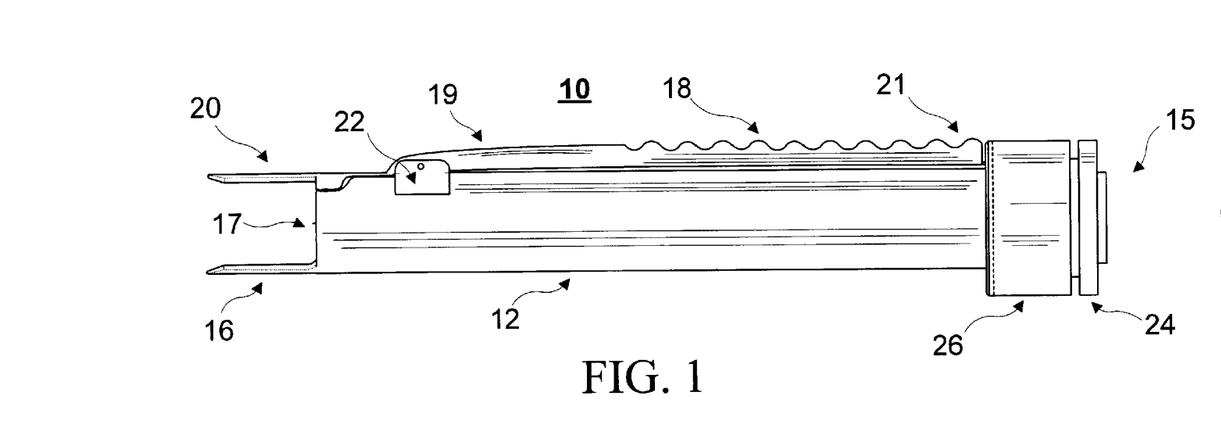
FIG. 1 shows a side view of a retracted spinal implant insertion instrument, according to one cylindrical form of the present invention.
Figure 1A:
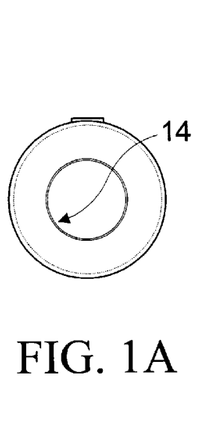
FIG. 1a shows an end view of a retracted spinal implant insertion instrument, according to one cylindrical form of the present invention.
Figure 2:
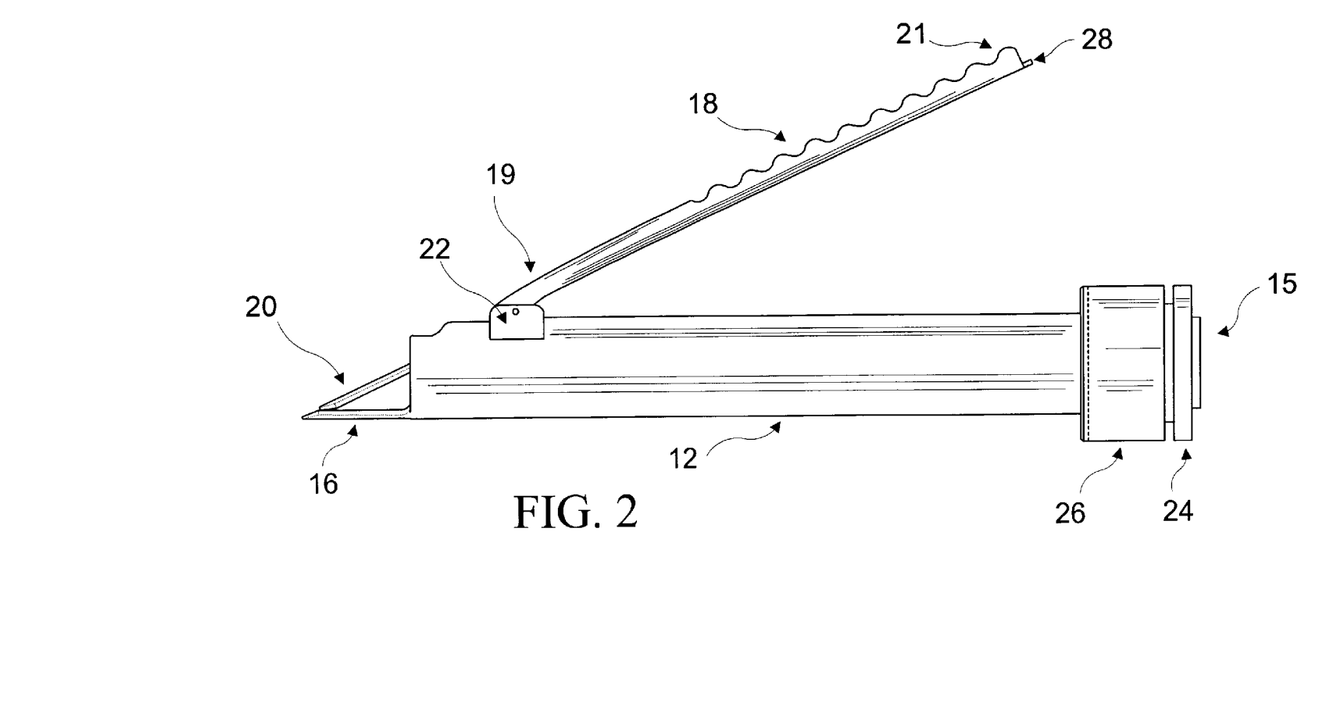
FIG. 2 shows a side view of an un-retracted spinal implant insertion instrument, according to one cylindrical form of the present invention.
Figure 3:
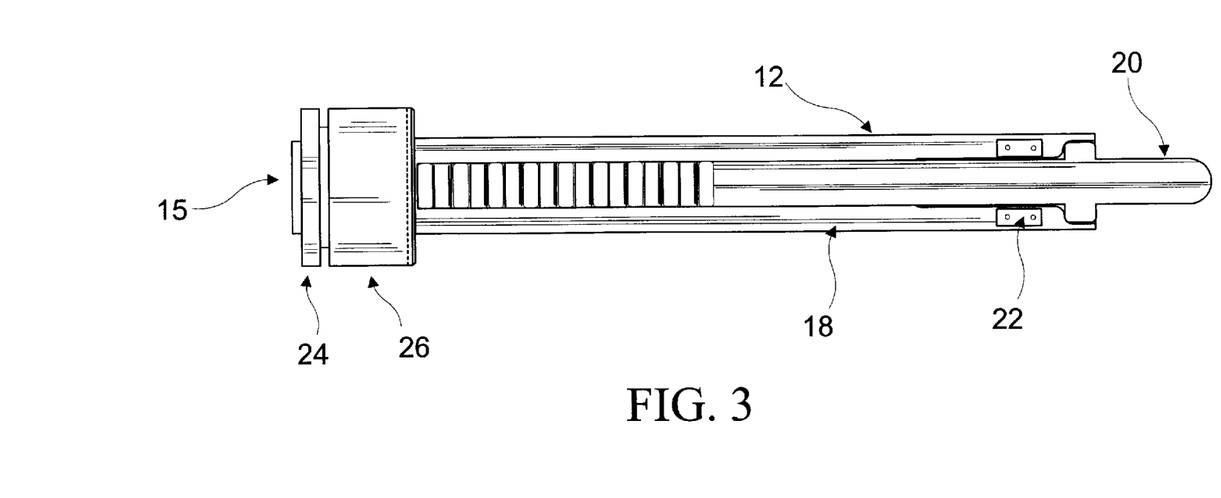
FIG. 3 shows a top view of a retracted spinal implant insertion instrument, according to one cylindrical form of the present invention.

Referring now in detail to the figures wherein like reference numbers represent like parts throughout, preferred forms of the present invention will now be described. As seen in FIGS. 1–3, one embodiment of the present invention comprises a spinal implant insertion instrument 10, generally comprising a hollow body 12 with an outer surface and an open interior surface 14. The insertion instrument 10 further comprises a distal end 17 and a proximal end 15 with a fixed conically shaped curved guide 16 extending from the distal end 17. Additionally, the insertion instrument 10 comprises a handle element 18 with a handle distal end 19 and a handle proximal end 21, with a retractable conically shaped curved guide 20 extending from the handle distal end 19.

The handle element 18 is pivotally attached to the hollow body 12, such that the conically shaped curved guides 16 and 20 are positioned on opposite sides of the hollow body 12. In a preferred embodiment, the handle distal end 19 is attached to the hollow body 12 distal end 17 by an articulating hinge 22. The articulating hinge 22, allows relative pivotal movement between the hollow body 12 and the handle element 18.

Figure 17:
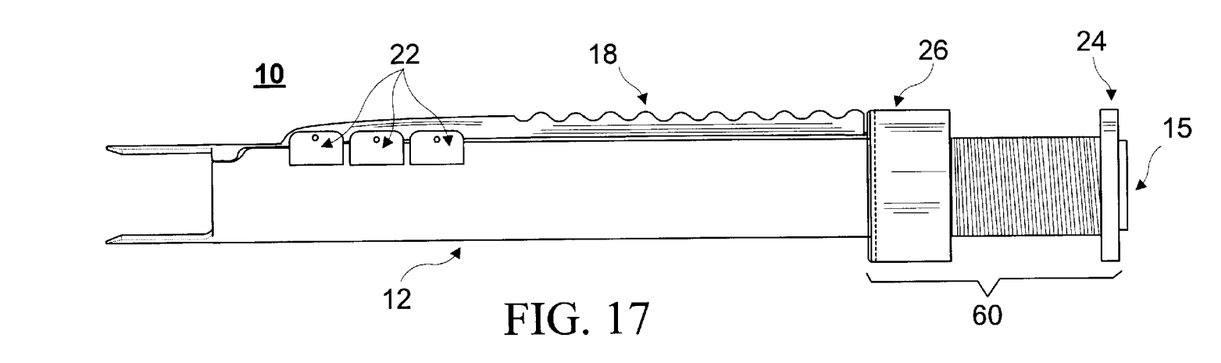
FIG. 17 shows a side view of a retracted spinal implant insertion instrument with vertically adjustable articulating hinges.
Figure 18:
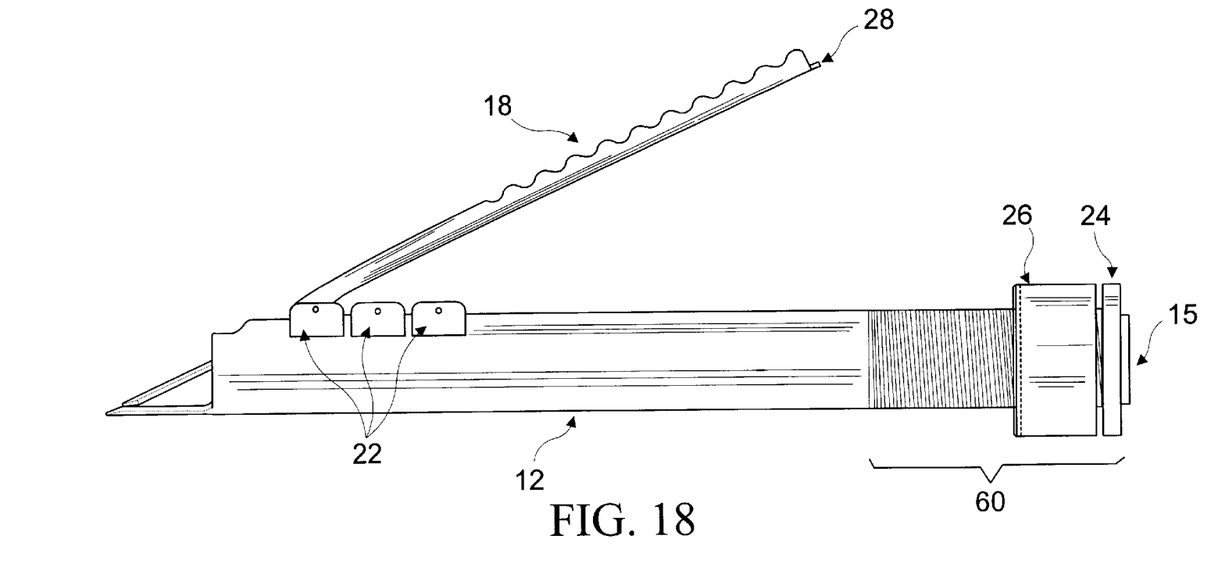
FIG. 18 shows a side view of a un-retracted spinal implant insertion instrument with vertically adjustable articulating hinges.

In an alternative embodiment, as shown in FIGS. 17 and 18, the articulating hinge 22 is vertically adjustable along the length of the hollow body 12 distal end 17. In an embodiment, the hollow body 12 distal end 17 comprises a plurality of articulating hinges 22. The handle 18 distal end 19 is removable attached to an articulating hinge 22 by an attachment pin. The insertion depth of the retractable curve guide 20 may be vertically adjusted by repositioning the handle 18 distal end 19 on to the desired articulating hinge 22.

Figure 11:
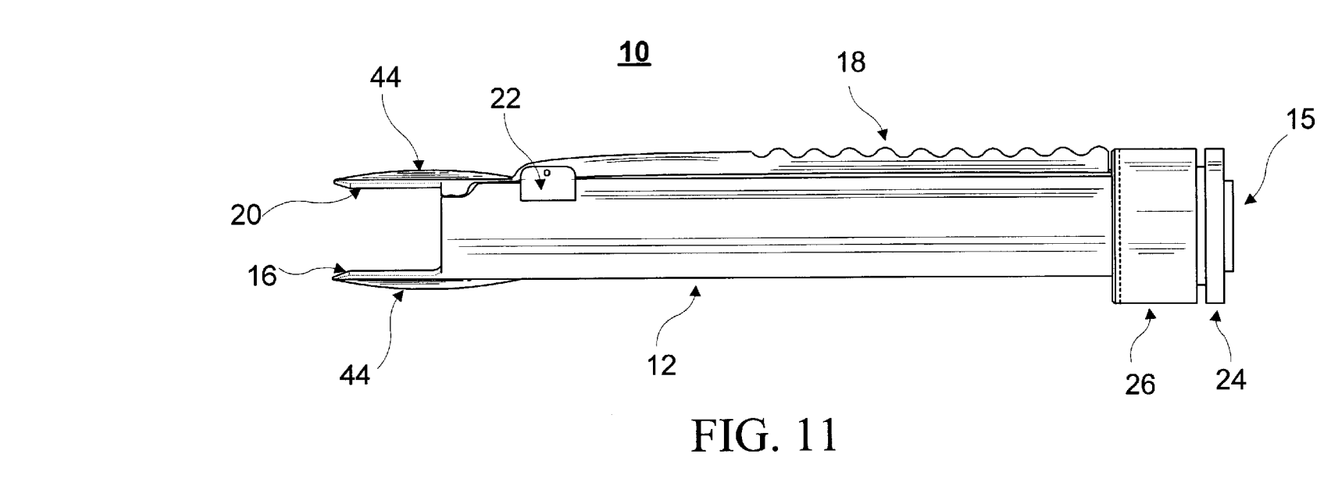
FIG. 11 shows a side view of the stringer elements on the fixed and retractable curved guides.
Figure 12:
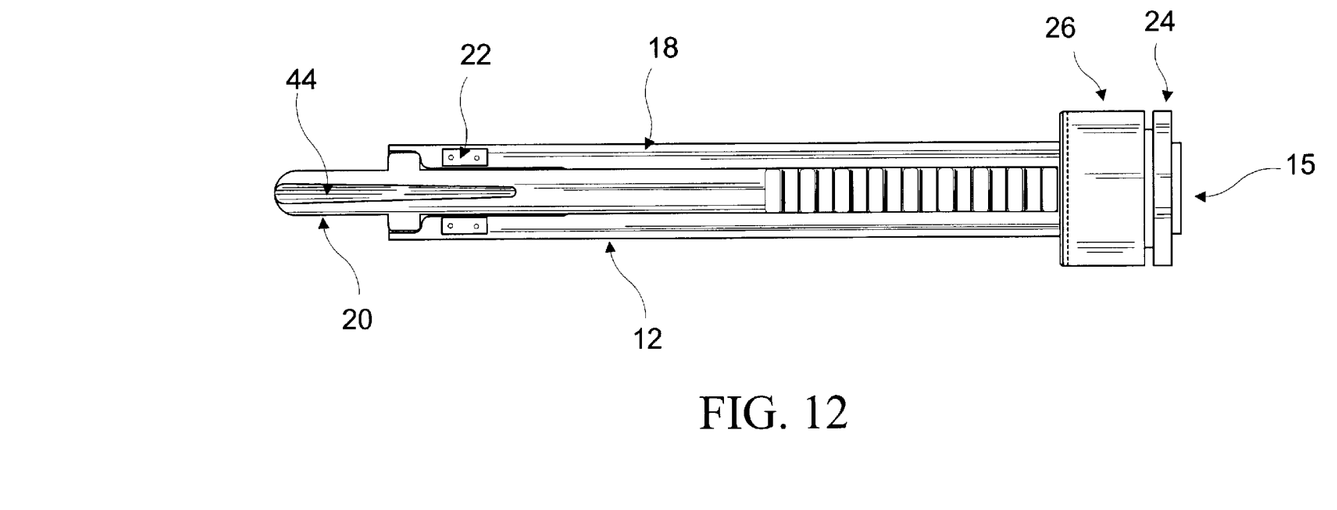
FIG. 12 shows a top view of the stringer elements on the retractable curved guide.

In an alternative embodiment, as shown in FIGS. 11 and 12, stringer elements 44 are affixed to the outer surface of the fixed curved guide 16 and to the outer surface of the retractable curved guide 20. The stringer elements 44 traverse the lengths of the curved guides 16 and 20, partially covering the distal end 17 of the hollow body 12 and the distal end 19 of the handle element 18, respectively. The outer surface of each stringer element 44 is sufficiently shaped so as not to cause trauma to the exposed nerves. In a preferred embodiment, the curved guides 16 and 20 are milled incorporating the stringer elements 44. In an alternative embodiment, the stringer elements 44 can be affixed to the curved guides 16 and 20 by welding, or other similar methods known in the art.

Figure 13:
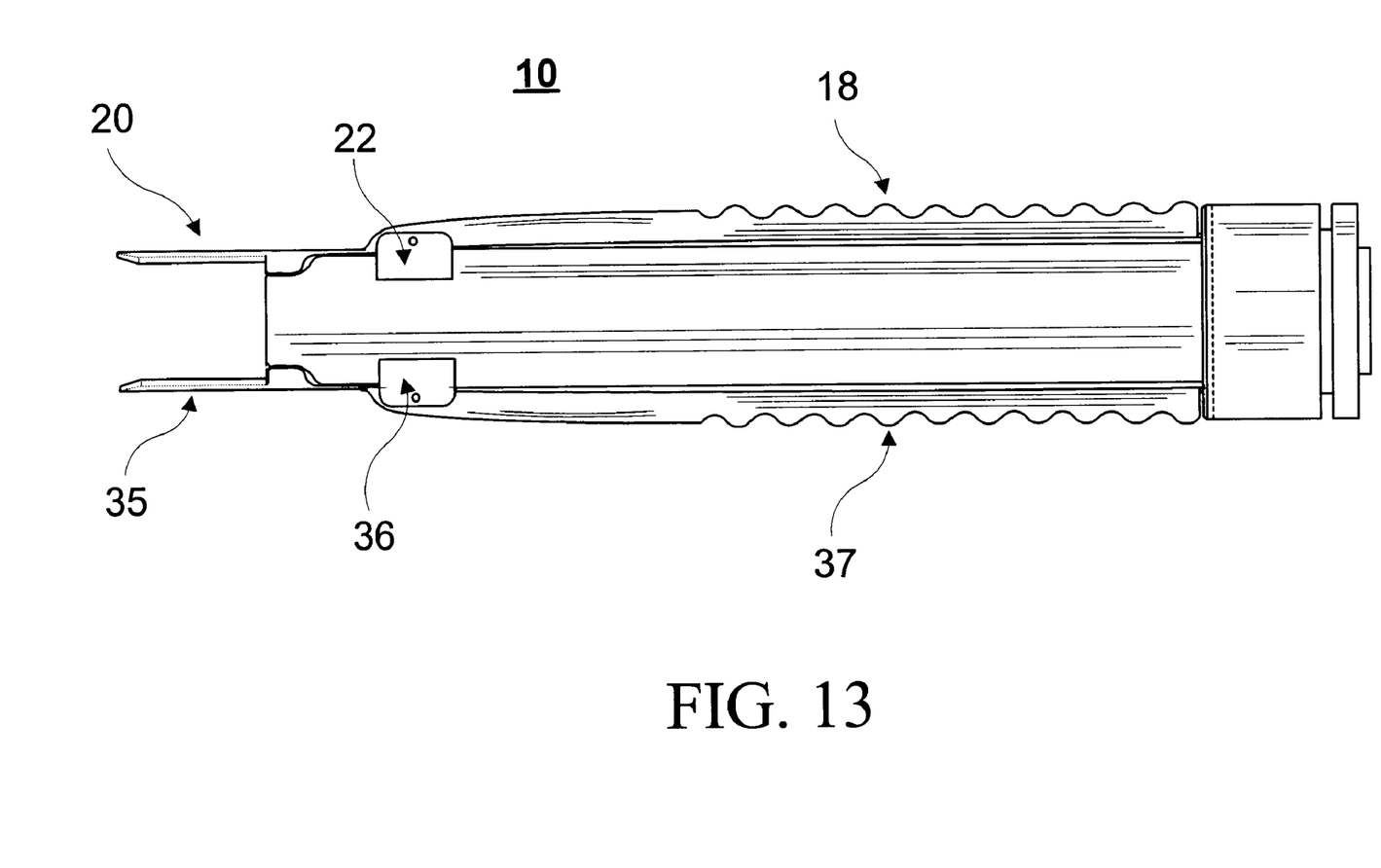
FIG. 13 shows a side view of a retracted spinal implant insertion instrument with two retractable curved guides.
Figure 14:
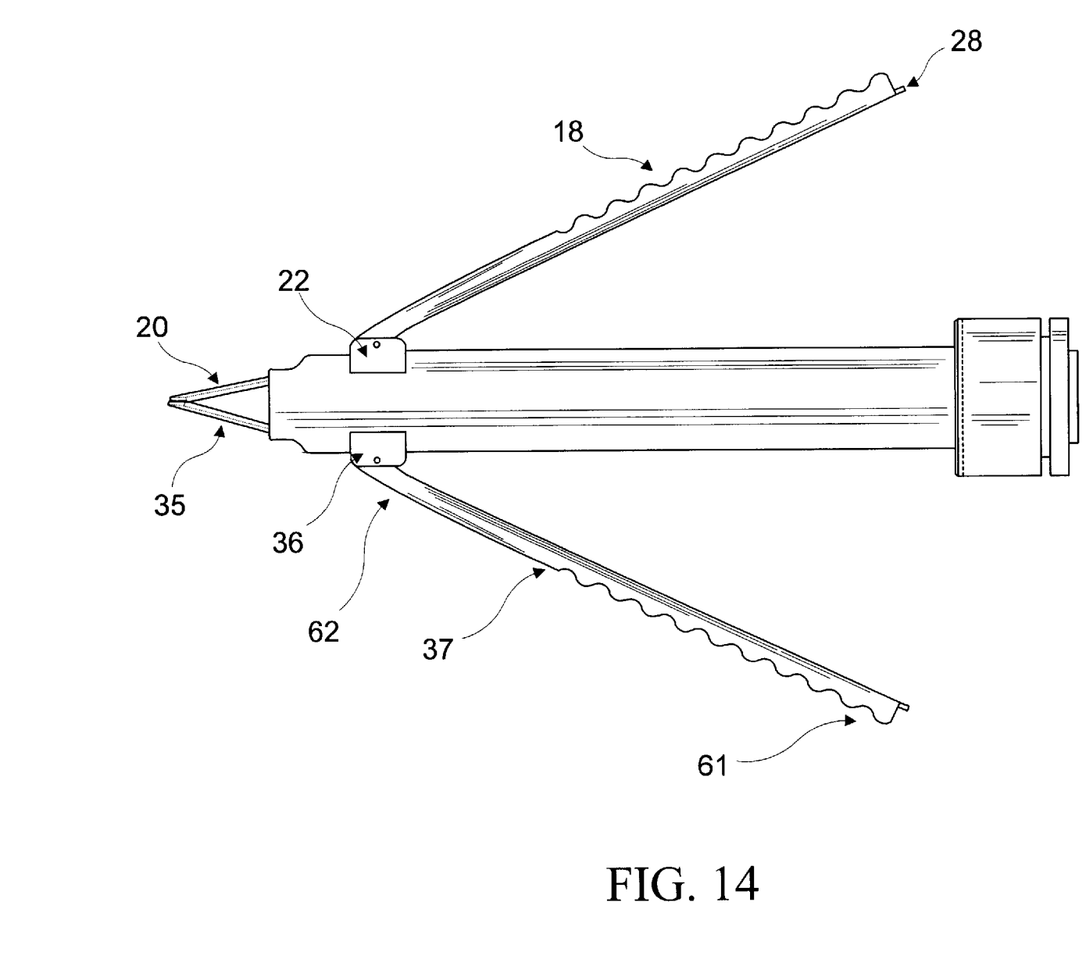
FIG. 14 shows a side view of an un-retracted spinal implant insertion instrument with two retractable curved guides.

In a further embodiment, as shown in FIGS. 13 and 14, the spinal implant insertion instrument 10 comprising a hollow body 12 with an outer surface, an open interior surface 14, a distal end 17, and a proximal end 15. The insertion instrument 10 further comprises a handle element 18 with a handle distal end 19 and a handle proximal end 21, with a retractable conically shaped curved guide 20 extending from the handle distal end 19. The handle element 18 is pivotally attached to the hollow body 12 at the distal end 17. The insertion instrument 10 comprises a second handle element 37, with a handle distal end 62 and a handle proximal end 61 with a second retractable conically shaped curved guide 35 extending from the handle distal end 62. The second handle element 37 is pivotally attached to the hollow body 12, such that the conically shaped curved guides 20 and 35 are positioned on opposite sides of the hollow body 12. In a preferred embodiment, the handle distal ends 19 and 62 are attached to the hollow body 12 distal end by articulating hinges 22 and 36. The articulating hinges 22 and 36 allow relative pivotal movement between the hollow body 12 and the handle elements 18 and 37.

The inner diameter of the hollow body 12 is of sufficient size to allow passage of instruments for vertebral cutting, reaming and tapping, and subsequent placement of intervertebral bone grafts and prosthetic devices. Preferably, the inner diameter of the hollow body 12 is between from about 6 millimeters and 24 millimeters.

In an alternative embodiment, the cross-sectional area of the hollow body 12 can be rectangular, elliptical or other shape, so long as it is of sufficient size to allow passage of instruments for reaming, tapping, and placement of intervertebral bone grafts and prosthetic devices.

Figure 4:
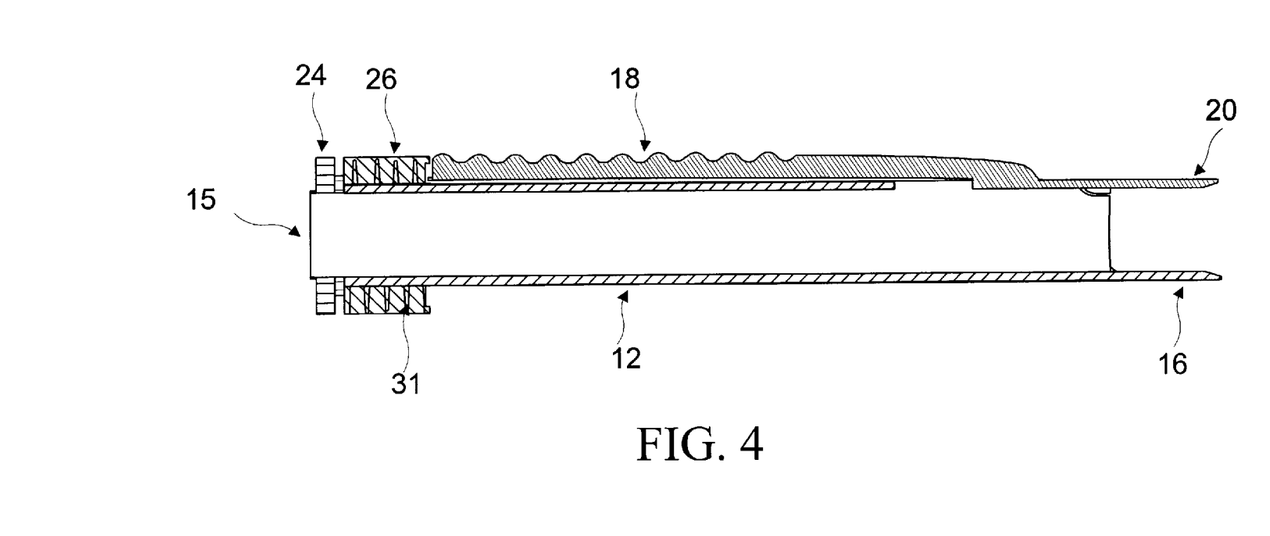
FIG. 4 shows a cross-sectional side view of a retracted spinal implant insertion instrument, according to one cylindrical form of the present invention.

In a further embodiment, an impact cap 24 and a primary locking mechanism 26 are located at the proximal end 15 of the hollow body 12. When engaged, the primary locking mechanism 26 secures the handle element 18 such that the guides 16 and 20 are in the fully extended position. In a preferred embodiment, as shown in FIG. 4, the primary locking mechanism 26 is a spring-loaded retraction ring 31, which locks and secures the handle element 18 by engaging a locking tab 28, which extends from the handle proximal end 21.

Figures 15, 16:
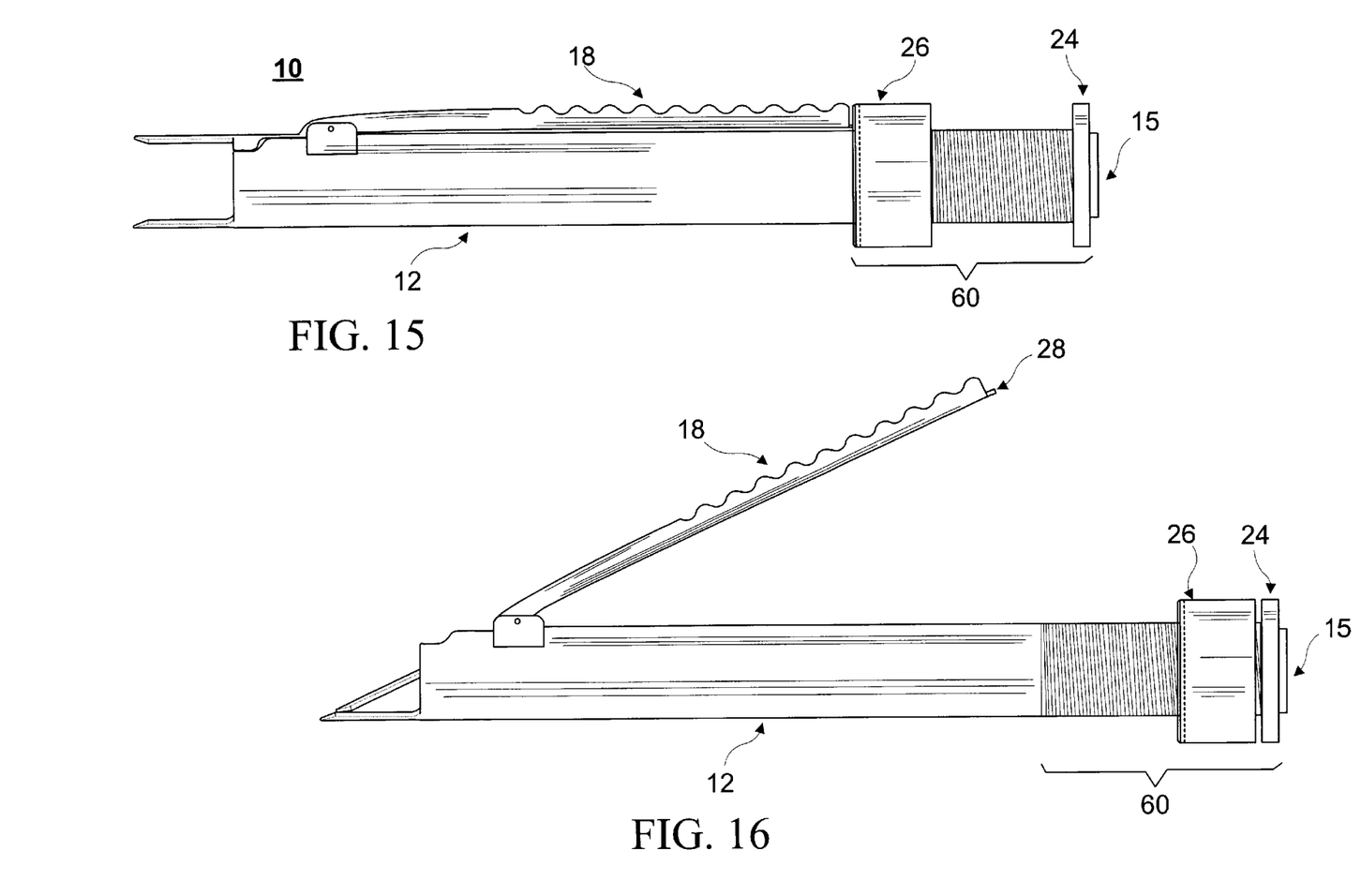
FIG. 15 shows a side view of a retracted spinal implant insertion instrument with a threaded locking means.
FIG. 16 shows a side view of an un-retracted spinal implant insertion instrument with a threaded locking means.

In an alternative embodiment, as shown in FIGS. 15 and 16, the handle element 18 is secured to the hollow body 12 by a threadably adjustable locking mechanism 60. The proximal end 15 of the hollow body 12 and the interior surface of the primary locking mechanism 26 are match threaded. The primary locking mechanism 26 secures the handle element 18 by threading the primary locking mechanism 26 onto the locking tab 28. The primary locking mechanism 26 releases the handle element 18 by threading the primary locking mechanism 26 off of the locking tab 28.

The spinal implant insertion instrument 10 can be fabricated from biocompatible materials including, without limitation, titanium, surgical alloys, stainless steel, or any other material suitable for fabrication of surgical instruments.

Figure 5:
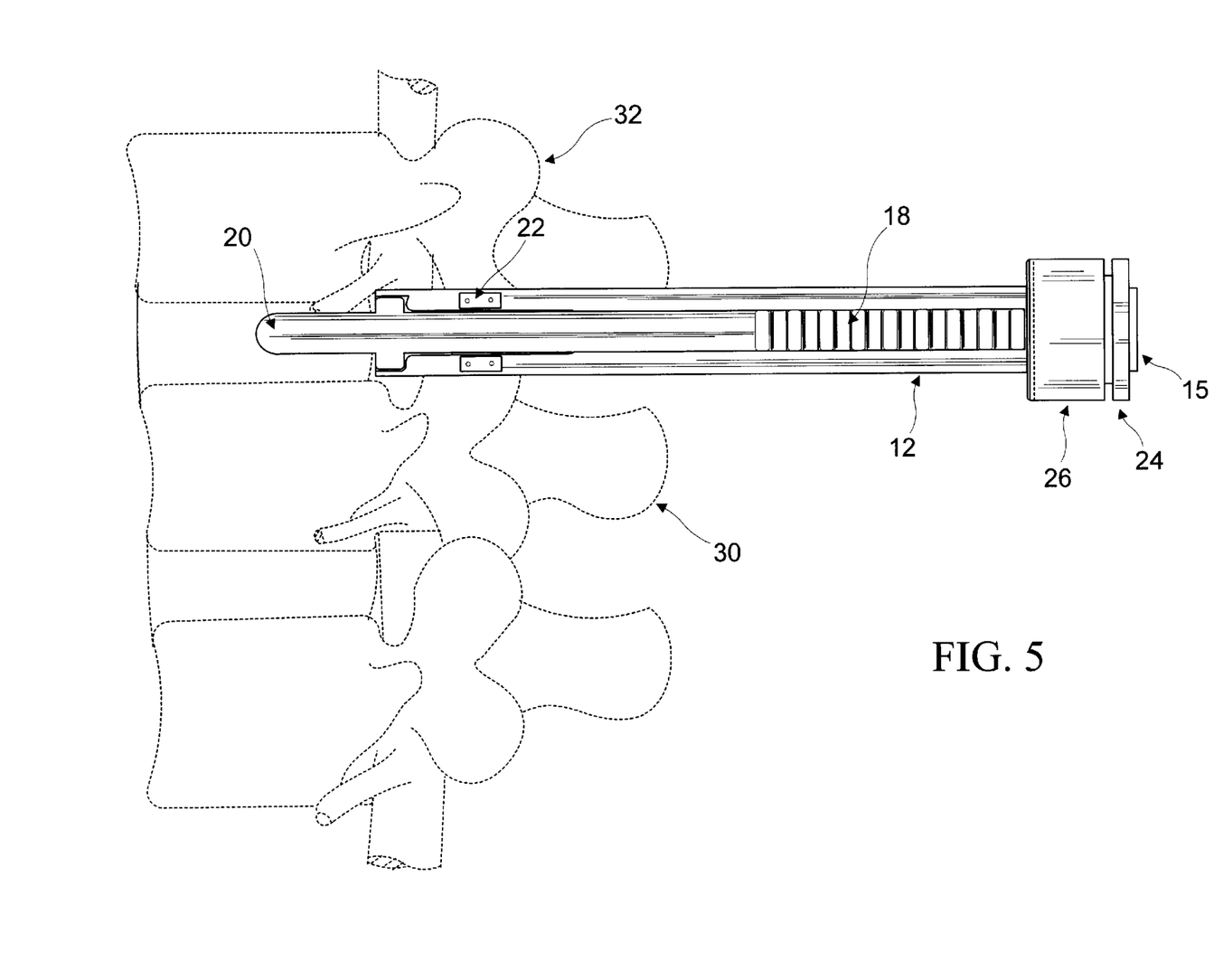
FIG. 5 shows a side view of the spinal implant insertion instrument in situ according to the cylindrical form of the present invention.
Figure 6:
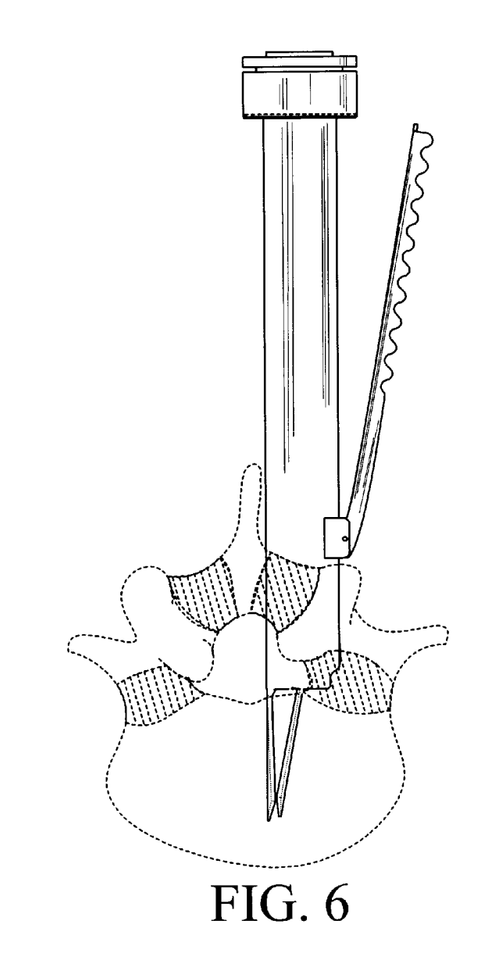
FIG. 6 shows a front view of the un-retracted spinal implant in situ according to the cylindrical form of the present invention.
Figure 7:
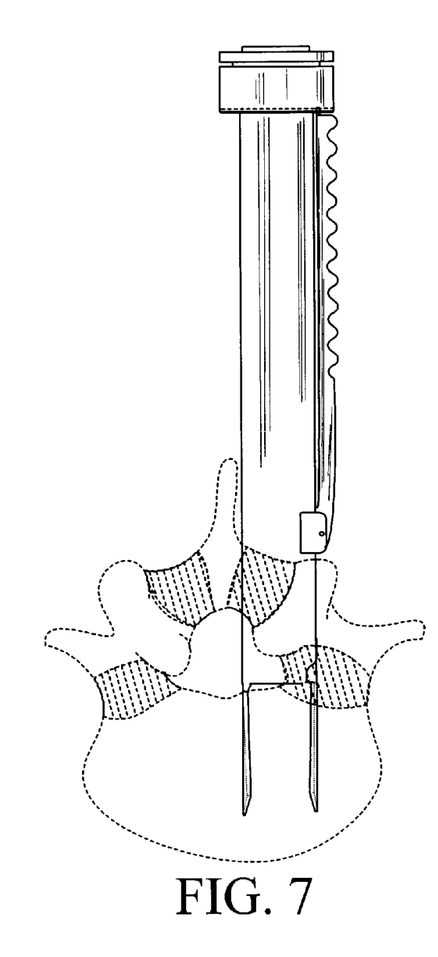
FIG. 7 shows a front view of the retracted spinal implant in situ according to the cylindrical form of the present invention.

In a preferred method of use, as shown in FIGS. 5–7, the curved guides 16 and 20 of the insertion instrument 10 are positioned between a first vertebra 30 and a second vertebra 32, with the curved guides 16 and 20 being in the un-retracted position. As shown in FIG. 6, the spinal implant 10 is inserted into the intervertebral space, in the un-retracted position, with the outer surface of the fixed curved guide 16 being positioned against the lumbar dural tube. The hinged joint 22 allows simultaneous retraction of the nerve root by compressing the handle element 18 into the hollow body 12. The simultaneous retraction of the nerve root away from the lumbar dural tube allows for a safe retraction of the neural elements, eliminating the need for an independent retraction means, which would add additional bulk in a confined space, which in the present art, contributes to inappropriate compression of neural elements. In the retracted position, the internal diameter of the hollow body 12 is sufficient to allow passage of instruments for cutting, reaming and tapping, and subsequent placement of intervertebral bone grafts and prosthetic devices.

Figure 8:
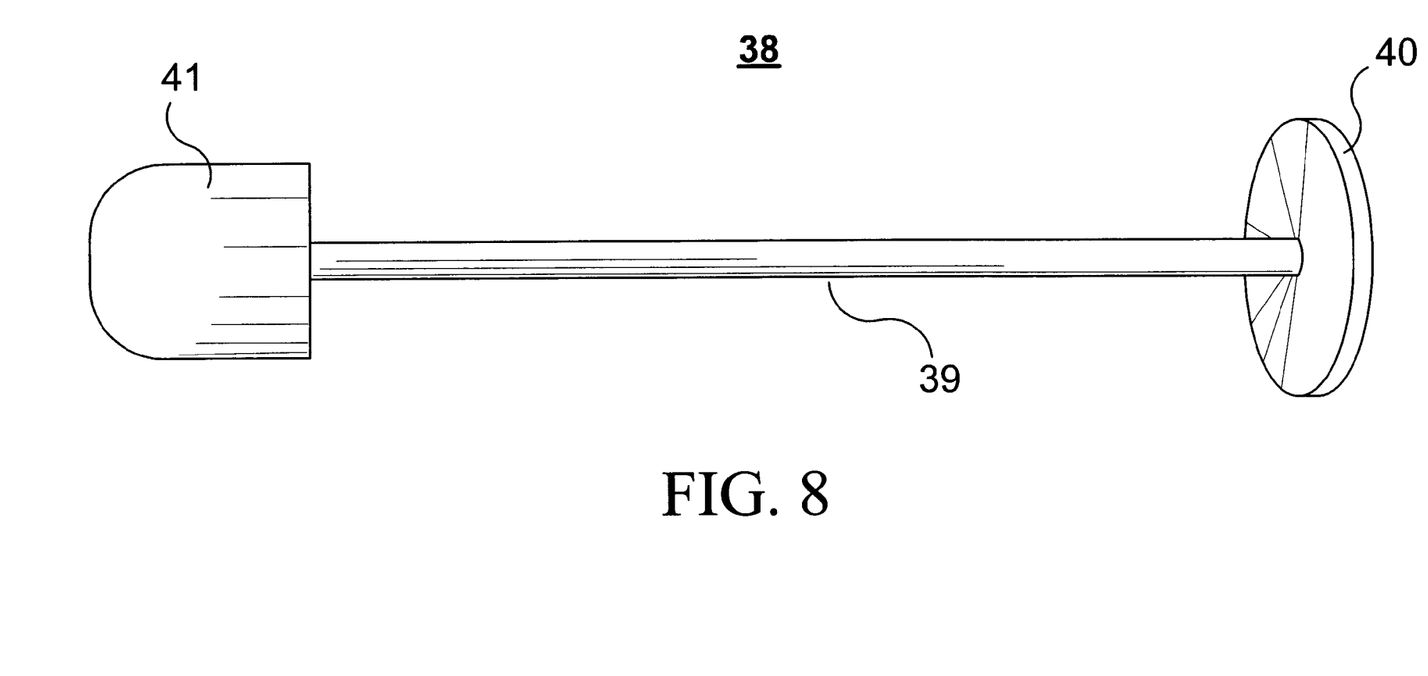
FIG. 8 shows a perspective view of the plunger to assist in the retraction of the retractable curved guide.

In a specific embodiment, a plunger 38, as shown in FIG. 8, can be inserted into the spinal implant insertion instrument 10 to assist in retracting the curved guides 16 and 20. The plunger comprises a shaft 39 with a stop 40 located at one end and a wedge 41 located at the opposite end. Once the curved guides 16 and 20 of the spinal implant insertion instrument 10 are positioned between a first vertebra 30 and a second vertebra 32, with the curved guides 16 and 20 being in the un-retracted position, the wedge 41 is inserted into the proximal end 15 of the hollow body 12. The plunger 38 is pushed through the hollow body 12 until the wedge 41 engages the curved guides 16 and 20. The curved guide 16 is retracted by simultaneously pushing the wedge 41 through the curved guides 16 and 20 and compressing the handle element 18 into the hollow body 12. The stop 40 prevents the wedge 41 from being pushed passed the curved guides 16 and 20. Once the handle element 18 is in the locked position, the plunger 38 is removed from the hollow body 12. The curved guide 16 can be locked in the retracted position to the curved guide 20 with a minimally larger snap lock flange along it's longitudinal axis.

Figure 9:
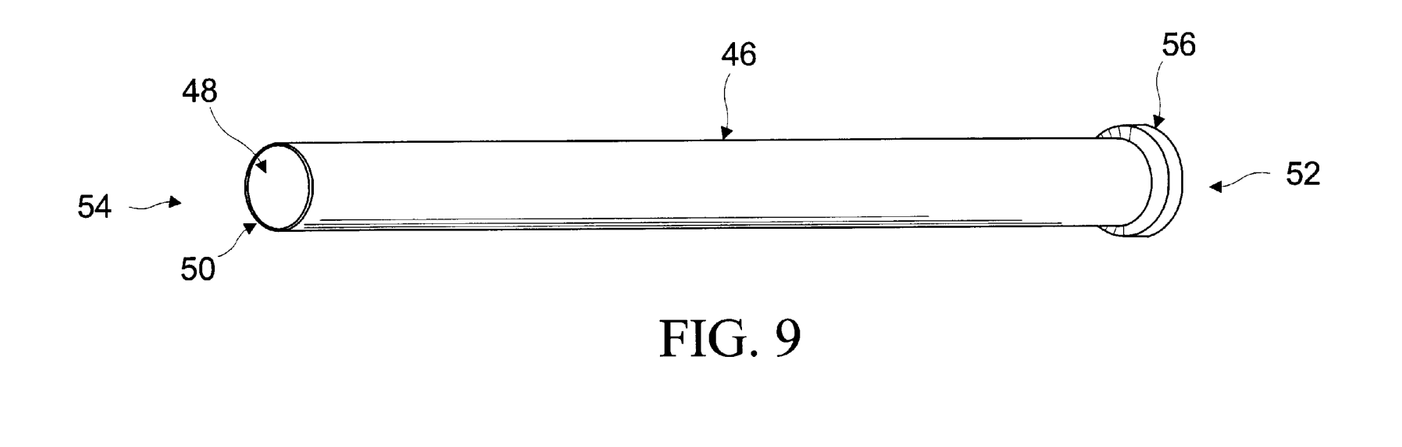
FIG. 9 shows a perspective view of the hollow guide element.
Figure 10:
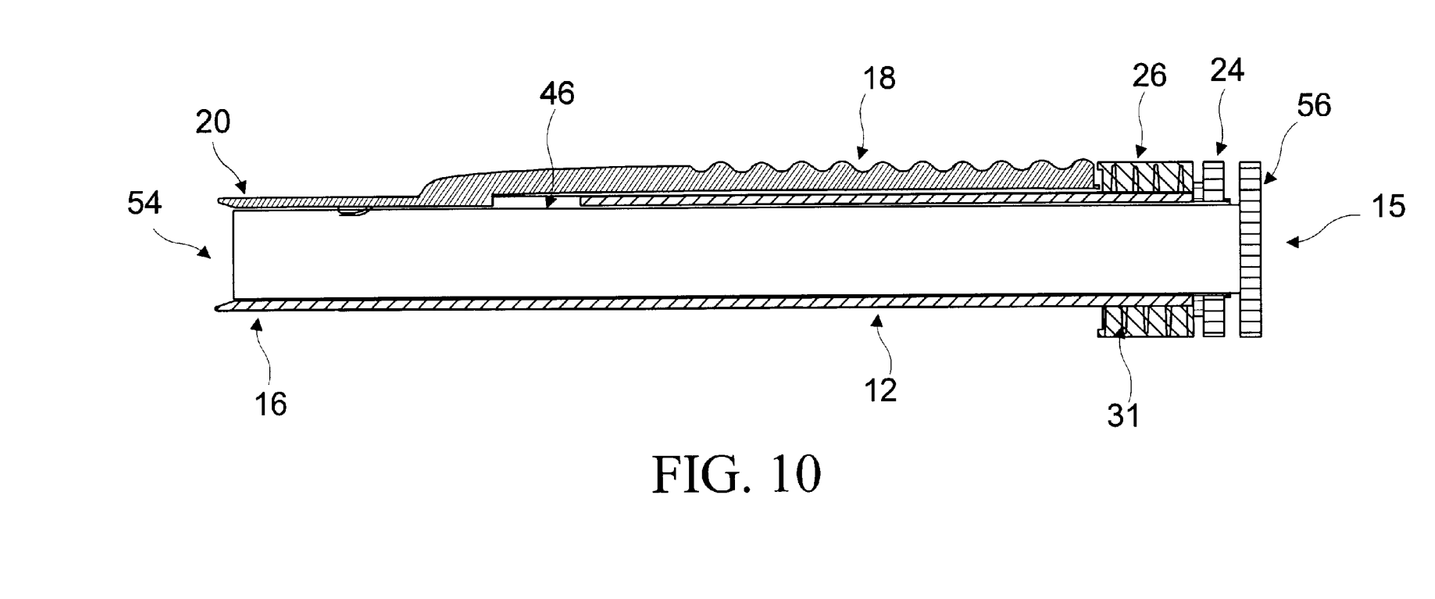
FIG. 10 shows a cut away side view of the hollow element inserted into the spinal implant insertion instrument.

In a further embodiment, as shown in FIGS. 9 and 10, a hollow guide element 46 is inserted into the hollow body 12. The hollow guide element 46 has an outer diameter 50 and an inner diameter 48, where the outer diameter 50 is slightly less than the inner diameter of the hollow body 12, such that the hollow guide element 46 can be inserted into the hollow body 12. The inner diameter 48 is of a size sufficient to allow passage of instruments for reaming, tapping, and subsequent placement of intervertebral bone grafts and prosthetic devices. A stop 56 is positioned at the top end 52 of the hollow guide element 46, limiting the hollow guide element's 46 travel distance. The length of the hollow guide element 46 is substantially equal to the length of the spinal insertion instrument 10. When the curved guides 16 and 20 are locked in the fully distracted position the bottom end 54 of the hollow guide element 46 is inserted into the proximal end 15 of the hollow body 12. In the fully inserted position the bottom end 54 of the hollow guide element 46 is positioned between the curved guides 16 and 20.

In an alternative embodiment, the cross-sectional area of the hollow guide element can be, for example, rectangular or elliptical in shape, matching the shape of the hollow body 12, and being any of a variety of sizes, sufficient to allow passage of instruments for reaming, tapping, and placement of intervertebral bone grafts and prosthetic devices.

In another embodiment, the spinal implant insertion instrument 10 can be more efficiently inserted by first introduction of a distraction tool. The distraction tool comprises a rectangular working surface, presenting first, the lesser dimension into the intervertebral disc space, and second, rotating the instrument so that the rotational action of the greater dimension distracts and moves apart the opposing vertebral surfaces preparatory to placement of the spinal implant insertion instrument into the center of the intervertebral disc space in it's retracted form. The spinal insertion instrument 10 can be inserted into the confined intervertebral disc space without undue retraction of neural elements, preparatory to placing the spinal implant insertion instrument into the intervertebral disc space in its retracted form.

Again, when fully deployed in the distracted state, the internal diameter of the insertion instrument 10 is restored to a sufficient radius to accommodate the previously-mentioned cutting, reaming, tapping, and spinal implant insertion instruments.

It should be understood that the examples and embodiments described herein are for illustrative purposes only, and various modifications or changes in light thereof will be suggested to persons skilled in the art and are to be included within the spirit and purview of this application.

What is claimed is:

1. A spinal implant insertion instrument comprising:
   a) a hollow body, wherein said hollow body comprises an outer surface, an inner surface, a proximal end, and a distal end;
   b) a first guide, wherein said first guide extends from said distal end of said hollow body,
   c) at least one handle element, wherein said handle element comprises a handle proximal end and a handle distal end; and
   d) at least one retractable guide, wherein said retractable guide extends from said handle distal end; wherein said handle distal end is hingedly attached to said distal end of said hollow body, such that said retractable guide opposes said first guide, wherein said instrument further comprises a hollow guide element comprising a top end, a bottom end, an inner diameter and an outer diameter, such that said hollow guide element can be inserted through said proximal end of said hollow body when said retractable guide is in a retracted position and said bottom end is positioned between said retractable guide and said first guide and said top end is positioned at said proximal end of said hollow body.

2. The spinal implant insertion instrument according to claim 1, wherein said first guide is a fixed guide.

3. The spinal implant insertion instrument according to claim 1, further comprising a locking means for locking said retractable guide in a retracted position.

4. The spinal implant insertion instrument according to claim 3, wherein said locking means comprises a spring-loaded retraction ring attached to the proximal end of said hollow body and a locking tab extending from said handle proximal end, wherein said spring-loaded retraction ring engages said locking tab, such that said retractable guide is locked in a retracted position.

5. The spinal implant insertion instrument according to claim 1, further comprising an impact cap positioned on said proximal end of said hollow body.

6. The spinal implant insertion instrument according to claim 1, wherein said outer diameter of said hollow guide element is slightly less than an inner diameter of said hollow body.

7. The spinal implant insertion instrument according to claim 1, wherein the geometric shape of a cross-sectional area of said hollow body is selected from the group consisting of circular, elliptical, and rectangular forms.

8. The spinal implant insertion instrument according to claim 1, wherein said hollow body has an inner diameter between about 6 mm to 24 mm.

9. The spinal implant insertion instrument according to claim 1, wherein said spinal implant insertion instrument is made of a biocompatible material.

10. The spinal implant insertion instrument according to claim 1, wherein said spinal implant insertion instrument is made of a material selected from the group consisting of titanium, stainless steel, and surgical alloys.

* * * * *

UNITED STATES PATENT AND TRADEMARK OFFICE
CERTIFICATE OF CORRECTION

PATENT NO.    : 6,520,967 B1
DATED         : February 18, 2003
INVENTOR(S)   : Joseph C. Cauthen It is certified that error appears in the above-identified patent and that said Letters Patent is hereby corrected as shown below:

<u>Title page,</u>
Item [57], ABSTRACT,
Line 9, "inteivertebral disc space" should read -- intervertebral disc space --
Line 16, "traction uponsensitive neural" should read -- traction upon sensitive neural --

<u>Column 6,</u>
Line 17, "guide clement can" should read -- guide element can --

Signed and Sealed this

Thirtieth Day of September, 2003

JAMES E. ROGAN
*Director of the United States Patent and Trademark Office*